United States Patent [19]

Merger et al.

[11] 4,375,000
[45] Feb. 22, 1983

[54] PROCESS FOR THE PREPARATION OF AN ARYL MONO-, DI-, AND/OR POLYURETHANE

[75] Inventors: Franz Merger, Frankenthal; Friedrich Towae, Ludwigshafen; Wolfgang Harder, Weinheim, all of Fed. Rep. of Germany

[73] Assignee: BASF Aktiengesellschaft, Ludwigshafen, Fed. Rep. of Germany

[21] Appl. No.: 135,242

[22] Filed: Mar. 31, 1980

[30] Foreign Application Priority Data

Apr. 30, 1979 [DE] Fed. Rep. of Germany ....... 2917568
Oct. 20, 1979 [DE] Fed. Rep. of Germany ....... 2942511

[51] Int. Cl.$^3$ ............... C07C 125/07; C07C 125/077; C07C 125/063
[52] U.S. Cl. ........................... 560/25; 560/24; 560/27; 560/28; 560/29; 560/30; 560/31; 560/32; 560/22; 560/21
[58] Field of Search ...................... 560/24, 25, 27, 28, 560/29, 30, 31, 32, 22, 21

[56] References Cited

U.S. PATENT DOCUMENTS 2,409,712 10/1946 Schweitzer ........................... 560/24
2,806,051 9/1957 Brockway ............................. 560/24

Primary Examiner—B. Helfin
Attorney, Agent, or Firm—David L. Hedden; Joseph D. Michaels

[57] ABSTRACT

A process for the preparation of an aryl mono-, di-, and/or polyurethane comprising the steps of A. reacting a primary aromatic mono-, di-, and/or polyamine with an O-alkyl carbamate in the presence of an alcohol at temperatures greater than 160° C., and B. separating the ammonia and other by-products from the aryl mono-, di-, and/or polyurethane.

The reaction is preferably carried out in the presence of urea. The aryl mono-, di-, and/or polyurethanes produced are valuable end and intermediate products. They can be transferred into the corresponding isocyanates which can then be used for the preparation of polyurethanes.

12 Claims, No Drawings

PROCESS FOR THE PREPARATION OF AN ARYL MONO-, DI-, AND/OR POLYURETHANE

BACKGROUND OF THE INVENTION

1. Field of the Invention

The invention pertains to the preparation of an aryl mono-, di- and/or polyurethane by reacting a primary aromatic mono-, di- and/or polyamine with an O-alkyl-carbamate in the presence of an alcohol. The reaction is preferably carried out in the presence of urea.

2. Description of the Prior Art

On an industrial scale, N-aryl urethanes are normally produced by the reaction of alcohols with isocyanates or by the reaction of amines with chlorocarbonates. The isocyanates and chlorocarbonates used in these reactions are obtained by phosgenation of the corresponding amines or the corresponding alcohols. Houben-Weyl, *Methods of Organic Chemistry*, Vol. 8, pages 137, 120 and 101, (Georg Thieme Publishers, Stuttgart, 1952). These processes are very expensive and phosgene must be used with care because of its potential danger to man and the environment.

N-aryl urethanes are used as intermediates and end products. For instance, German Published Application 26 35 490 and U.S. Pat. No. 3,919,278 disclose the use of N-substituted urethanes for the manufacture of isocyanates. Because of their utility, many attempts have been made to develop better methods for preparing N-substituted urethanes. These methods and their shortcomings will be discussed.

German Published Application 21 60 111 describes a process for the manufacture of N-substituted urethanes by reacting an organic carbonate with a primary or secondary amine in the presence of a Lewis acid. There are several problems with this process. The conversion rates are rather low and the reaction times are long. Furthermore, N-alkylarylamines are always produced as by-products.

U.S. Pat. No. 2,834,799 describes a process for making carbamic and carbonic esters by the reaction of urea with alcohols in the presence of boron trifluoride. The problem with this method is that the boron trifluoride is required in equimolar quantities so that at least one molecule of boron trifluoride is used per molecule of produced carbamic ester and at least two molecules of boron trifluoride are consumed per molecule of carbonic ester. This process is not only expensive, but it causes problems in the environment because the boron trifluoride is produced in the form of the $H_3N.BF_3$ adduct.

R. A. Franz et al. *Journal of Organic Chemistry*, Vol. 28, page 585 (1963) describe a process for making methyl-N-phenyl urethane from carbon monoxide, sulfur, aniline, and methanol. Very low yields are produced by this method; the yield does not exceed 25 percent even when there is a long reaction period.

U.S. Pat. No. 2,409,712 describes a process for making N-alkyl and N-aryl urethanes by the reaction of monoamines with urea (either N,N'-dialkyl- or N,N'-diarylurea is used) and alcohols at temperatures of 150° C. to 350° C. under increased pressure. It should be noted that this patent only describes the manufacture of N-alkylmonourethanes and does not mention the manufacture of N,N'-disubstituted diurethanes and polyurethanes. U.S. Pat. No. 2,677,698 also describes a process for the manufacture of N-substituted monourethanes. In this process, the urea is initially converted into the corresponding N,N'-disubstituted urea with monoamines, is then cleaned, and subsequently is reacted with an alcohol. The processes described are expensive and the yields are very low. Attempts to improve the yield by improving the methods of preparing and purifying the N,N'-disubstituted ureas have been unsuccessful.

Other processes have not been successful in eliminating the problems described thus far. U.S. Pat. No. 2,806,051 describes a process whereby N-substituted urethanes are produced by reacting aniline with urea and alcohol at a mole ratio of 1.0:1.2:2.0 at temperatures below 200° C., preferably of 120° C. to 160° C. Even in the preferably used temperature range, this process produces only small yields of N-substituted urethanes if the reaction time is limited to a period which is practical in an industrial setting. In view of the problems with this process, it is not surprising that U.S. Pat. No. 3,076,007, which describes the manufacture of N-alkyl and N-cycloalkyl urethanes, does not incorporate the above-referenced methods in its process. It does, however, describe the reaction of phosgene with alcohols to form chloroalkylformates, and it describes their subsequent reaction with amines to form urethanes. It also discloses the reaction of amines with ethylene carbonate to form urethanes. German Published Application 27 16 540 describes a more recent variation of this process wherein aromatic urethanes are prepared by reacting dialkyl carbonates with N-ethyl amines.

It is also known that ethyl carbamates do not react with amines in boiling dioxane [D. G. Crosby and C. Niemann, *Journal of the American Chemical Society*, Vol. 76, page 4458 (1954)], and that the reaction of N-alkyl urethanes with alcoholic ammonia solutions at temperatures of 160° C. to 180° C. result in an alkali solution from which aminohydrochloride, urea, alkylurea and alkyl urethane can be isolated by means of hydrochloric acid after neutralization [M. Brander, *Rec. trav. Chim.*, Vol. 37, pages 88–91 (1917)]. The referenced publications do not contain any disclosure concerning the reaction of aromatic primary amines with carbamates although it is known that the heating of ethyl carbamate with aniline at 160° C. in a bomb tube will produce diphenylurea. See Annalen, Vol. 147, page 163 (1868).

U.S. Pat. No. 2,409,712, discloses that the reaction of aliphatic monoamines, urea and alcohol will produce alkyl urethanes. However, only small yields result even though excess urea is used. Since somewhat higher yields are achieved with less urea and at lower temperatures according to U.S. Pat. No. 2,806,051, one has to assume that higher mole ratios of urea to amines are disadvantageous. Diphenylurea and O-alkyl carbamate were determined as by-products of the synthesis of phenylurethane. The O-alkyl carbamate was isolated by means of distillation in addition to unreacted aniline. The formation of O-alkyl carbamate from urea and alcohol was therefore considered as an interferring secondary reaction. Since even the manuacture of N-monoalkylsubsituted urethanes from alkylamines, urea, and alcohols succeeds with moderate yields only, and since carbamates are produced as by-products, it is not surprising that the prior art does not teach the preparation of aryl mono-, di- and/or polyurethanes from arylamines and O-alkyl carbamates.

Because of the problems identified thus far, other methods of producing N-arylurethanes have been tried. Some have suggested that N-arylurethanes can be prepared by reacting nitroaromatics with carbon monoxide, and alcohols in the presence of catalysts. German Published Application 15 68 044 (U.S. Pat. No. 3,467,694) teaches that urethanes may be prepared by the reaction of organic nitro compounds, carbon monoxide, and hydroxyl-containing compounds in the presence of a catalysts consisting of a noble metal and a Lewis acid under essentially anhydrous conditions in the absence of hydrogen under increased pressure and at temperatures above 150° C. German Published Application 23 43 826 (U.S. Pat. No. 3,895,054) teaches that urethanes can be prepared from hydroxyl group-containing compounds, carbon monoxide, and nitro-, nitroso-, azo- and azoxy group-containing compounds in the presence of sulfur, selenium, a sulfur and/or selenium compound and at least one base and/or water. German Published Application 26 23 694 (U.S. Pat. No. 4,080,365) describes the preparation of aromatic urethanes from the above-referenced starting compounds in the presence of selenium-containing catalyst systems as well as special aromatic amino and urea compounds. However, the use of these processes involve serious drawbacks. The toxic carbon monoxide and catalysts which are toxic or form toxic compounds during the reaction, such as hydrogen selenide and hydrogen sulfide, or catalysts which are very expensive and are difficult to recycle such as palladium, require great technical expenditure and costly safety measures.

None of the references cited discloses the preparation of aryl mono, di and/or polyurethane by reacting an aromatic amine with an O-alkyl carbamate in the presence of an alcohol at temperatures greater than 160° C. Moreover, the processes described all involve several disadvantages. It is surprising that aryl mono, di and/or polyurethanes can be produced in one process stage with good yields by reacting carbamates with primary aromatic amines in the presence of an alcohol at temperatures greater than 160° C. Prior teachings indicate that corresponding diureas are obtained from diamines and carbamates; for example, hexamethylenediurea is obtained from hexamethylenediamine and carbamates. Prior art also teaches that, although urea and alcohol may react to produce urethanes, they continue to react to form N,N'-disubstituted ureas in the presence of amines. See Houben-Weyl, *Methods of Organic Chemistry*, Vol. 8, pages 152, 140, and 161, (Georg Thieme Publishers, Stuttgart, 1952). These side reactions decrease the yield of the desired product.

Furthermore, German Patent 896 412 indicates that high molecular, spinnable condensation products may be produced from the diamides of carbonic acid such as urea and diamines. This result is likely to occur if the amino groups of the diamines are separated by a chain of more than three atoms. U.S. Pat. Nos. 2,181,663 and 2,568,885, for instance, disclose that high molecular polyureas with molecular weights of 8000 to 10,000 and greater, may be produced when diurethanes are condensed with diamines at temperatures of approximately 150° C. to 300° C. Moreover, mono- and polyurethanes can be split thermally into isocyanates, alcohols and possibly olefins, carbon dioxide, urea and carbodiimide, and these products can be split into products such as biurets, allophanates, isocyanurates, polycarbodiimides, and others. See *The Journal of the American Chemical Society*, Vol. 80, page 5495 (1958) and Vol. 48, page 1946 (1956).

In view of the problems disclosed in the prior art, it was surprising that our process, which involved very similar reaction conditions, would result in mono, di- and/or polyurethane with very good yields. It was particularly surprising because when diurethanes were prepared from the products mentioned in the previous paragraph according to the reaction conditions of our invention, good yields did not result.

SUMMARY OF THE INVENTION

The purpose of this invention was to produce an aryl mono-, di-, and/or polyurethane from readily available raw materials in one reaction stage under economically justifiable conditions with good yields. The use of strongly toxic raw materials such as phosgene, carbon monoxide, or catalysts which are toxic and form toxic compounds during the reaction, such as hydrogen sulfide, was to be avoided.

The problem was solved by developing a process for the preparation of the aryl mono-, di-, and/or polyurethanes comprising the steps of A. reacting a primary aromatic mono-, di-, and/or polyamine with an O-alkyl carbamate in the presence of an alcohol at temperatures greater than 160° C., and B. separating the ammonia and other by-products from the aryl mono-, di-, and/or polyurethane.

The reaction may be illustrated by the following equation I:

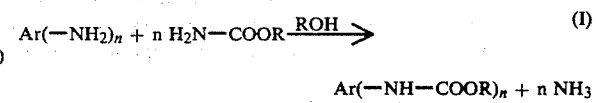

However, the reaction is preferably carried out in the presence of urea according to equation (II):

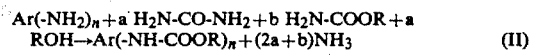

In equations (I) and (II), n, a, and b represent whole numbers with n standing for 1–7, preferably 1–5, and with a+b, according to equation (II), equaling n and a:n equaling 1.5–0.

The aryl mono-, di-, and/or polyurethanes produced according to the process of this invention are valuable end and intermediate products. They are used, for instance, as pesticides. As intermediate products, they are used as components for polycondensation and polymer systems and, in particular, they are transformed into the corresponding di- and/or polyisocyanates by removal of the alcohol. The di- and/or polyisocyanates can be used in the manufacture of polyurethanes.

Description of the Preferred Embodiments

In order to prepare the aryl mono-, di-, and/or polyurethane in accordance with the process of this invention, a primary aromatic mono, di, and/or polyamine is reacted with an O-alkyl carbamate in the presence of alcohol in such quantities that the ratio of amino groups of the primary aromatic amines to O-alkyl carbamates to hydroxyl groups of the alcohol is 1:0.5–20:1–100, preferably 1:0.8–10:1–50 and especially for arylmonourethanes, 1:1–6:1–5, and for aryl-di- and/or polyurethanes, 1:1–6:2–30. The reaction preferably is carried out in the presence of urea.

It is not necessary to separately produce O-alkyl-carbamates in a preceeding process stage. In an easily practiced, preferably used version, the O-alkyl carbamate is used together with urea and alcohol, and after extensive to complete reaction of the aromatic mono- and/or polyamines, the O-alkyl carbamate is separated by means of distillation and is recycled if so required. The process according to this invention may also be conducted in a continuous phase.

Unsubstituted or substituted primary aromatic mono-, di- and polyamines are suited for the reaction with the O-alkyl-carbamate in the presence of alcohol and in the presence or absence of urea according to this invention. Representative amines include the following: aromatic monoamines such as aniline, substituted aniline, such as anilines substituted in the 2, 3 and/or 4 position by a nitro-, methyl-, n-propyl-, isopropyl-, n-butyl-, isobutyl-, secondary butyl-, tertiary butyl group or a chlorine atom; ortho-, meta- and/or parahydroxy-, methoxy-, ethoxy-, propoxy-, isopropoxy-, N-butoxy-, isobutyoxy-, secondary butoxy-, and tertiary butoxyaniline; an alkylbenzoate with 1 to 4 carbon atoms in the alkyl radical substituted by an amino group in the n- and/or p-position; N-alkoxycarbonylaminobenzenes and -toluenes with 1 to 4 carbon atoms in the alkyl radical substituted by an amino group in the m- and/or p-position; alpha- and beta-naphthalamine; aromatic diamines such as 1,3- and 1,4-diaminobenzene; aromatic diamines such as 1,3- and 1,4-diaminobenzene; 1,3-diaminobenzene substituted in the 2 and/or 4 position by nitro, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy groups or halogen atom, preferably fluorine or chlorine; or 1,4-diaminobenzene, 1,5- and 1,8-diaminonaphthalene, 4,4'-diaminodiphenyl, 2,2'-, 2,4'- and 4,4'-diaminodiphenylmethane and the corresponding isomer mixtures thereof, all of which may be substituted in the 2 position by a nitro, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy group or a halogen atom, preferably a fluorine or a chlorine atom; and aromatic polyamines such as 1,3,5-triaminobenzene, 2,4,6-triaminobenzene, 1,3,5-triaminobenzene, polyphenylpolymethylene polyamines as well as mixtures of diaminodiphenyl methanes and polyphenylpolymethylene polyamines which are produced in accordance with familiar methods by the condensation of aniline and formaldehyde in the presence of preferably mineral acids as catalysts and which may be substituted with any of the above identified groups or atoms.

The following compounds are preferably used as aromatic monoamines: o-, m- and/or p-toluidine, o-, m- and/or p-anisidine, 3-hydroxyaniline, o-, m- and/or p-chloroaniline, 2,4-, 3,4- and 3,5-dichloroaniline, 2-nitro-4-aminotoluene, 4-nitro-2-aminotoluene, 2-nitro-6-amino-toluene, and N-alkoxycarbonylarylamines having the formula

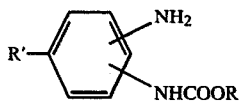

in which R represents a methyl-, ethyl-, propyl-, isopropyl-, n-butyl-, isobutyl-, secondary butyl-, or tertiary butyl-radical and in which R' stands for a hydrogen atom or the radical R as well as particularly aniline, 3,3'-ditolulene-4,4'-diamine, 2,4- and 2,6-tolulenediamine as well as the corresponding isomer mixtures, 2,2'-, 2,4'- and 4,4'-diaminodiphenylmethane and the corresponding isomer mixtures, 1,5- and 1,8-naphthalenediamine as aromatic diamines and mixtures of diaminodiphenylmethanes and polyphenylpolymethylene polyamines as polyamines. During the reaction, the amino groups are transformed into alkoxycarbonylamino groups independent of whether or not the remaining substituents remained unchanged or are also converted.

Suitable O-alkylcarbamates for the reaction have the formula $H_2N\text{-}COOR$ in which R represents an unsubstituted or substituted aliphatic, cycloaliphatic or aromatic-aliphatic radical. Representative examples include O-alkyl carbamates based upon primary aliphatic monoalcohols having 1 to 20 carbon atoms, preferably 1 to 10 carbon atoms such as methyl carbamate, ethyl carbamate, propyl carbamate, n-butyl carbamate, isobutyl carbamate, 2- and 3-methylbutyl carbamate, neopentyl carbamate, pentyl carbamate, 2-methylpentyl carbamate, n-hexyl carbamate, 2-ethylhexyl carbamate, heptyl carbamate, n-octyl carbamate, n-nonyl carbamate, n-decyl carbamate and n-dodecyl carbamate, 2-phenylpropyl carbamate and benzyl carbamate; and O-alkyl carbamates based upon secondary aliphatic and cycloaliphatic monoalcohols having 3 to 15 carbon atoms, preferably 3 to 6 carbon atoms such as isopropyl carbamate, secondary butyl carbamate, secondary isoamyl carbamate, cyclopentyl carbamate, cyclohexyl carbamate, tertiary butylcyclohexyl carbamate, and bicyclo-(2,2,1)-heptyl carbamate. Preferably used are methyl carbamate, ethyl carbamate, propyl carbamate, butyl carbamate, isobutyl carbamate, 2- and 3-methylbutyl carbamate, pentyl carbamate, hexyl carbamate, 2-ethylhexyl carbamate, heptyl carbamate, octyl carbamate, and cyclohexyl carbamate.

Unsubstituted or substituted primary or secondary aliphatic alcohols as well as mixtures thereof may be used as alcohols. Preferably used is the alcohol corresponding with the O-alkyl carbamate. Representative examples include primary aliphatic alcohols having 1 to 20 carbon atoms, preferably 1 to 10 carbon atoms, such as methanol, ethanol, propanol, n-butanol, 2-methylbutanol, n-pentanol, neopentylalcohol, 2-methylpentanol, n-hexanol, n-heptanol, n-octanol, nonanol, n-decanol, and n-dodecanol; and secondary aliphatic and cycloaliphatic alcohols having 3 to 15 carbon atoms, preferably 3 to 6 carbon atoms, such as isopropanol, secondary butanol, secondary isoamylalcohol, cyclopentanol, 2-, 3- or 4-methylcyclohexanol, cyclohexanol, and bicyclo-(2,2,1)-heptanol. Preferably used as monoalcohols are methanol, ethanol, propanol, n-butanol, isobutanol, 2-ethylbutanol, 2- and 3-methylbutanol, n-pentanol, n-hexanol, 2-ethylhexanol, heptanol, octanol and cyclohexanol. If required, the alcohols may be mixed with other organic solvents which are inert under the reaction conditions.

As already indicated, a preferred process version uses urea in addition to the O-alkyl carbamate for the manufacture of the aryl mono- and/or polyurethanes with the ratio of amino groups of the aromatic amines to the total of O-alkyl carbamate and urea also being 1:0.5-20, preferably 1:0.8-10, and particularly 1:1-6 with the mole ratio of urea to amino groups of the primary, aromatic amines being equal to or less than 1.5, preferably 1.25-0.75, and the mole ratio of urea to hydroxyl groups of the alcohol being equal to or less than 1. The urea is appropriately used in commercially-available form and purity.

The reaction is carried out at increased temperatures, for instance at temperatures of 160° C. to 300° C., preferably of 170° C. to 230° C., and particularly of 175° C. to 210° C., and under pressures of 0.1 bar to 120 bars, preferably 0.5 bar to 60 bars, and particularly 1 bar to 40 bars. The appropriate reaction time for the corresponding temperature ranges are 0.5 hour to 100 hours, preferably 1 hour to 50 hours, and particularly 2 hours to 25 hours. With a given temperature, the reaction is then preferably carried out under a pressure at which the resultant ammonia can be removed selectively from the reaction mixture by means of distillation. The corresponding values are contained in tables with the physical characteristics of ammonia and alcohols.

An advantageous way of preparing the aryl mono-, di-, and/or polyurethanes is to mix the reactants in the indicated quantity ratios and heat them in a reactor equipped with a device for separating the ammonia, possibly while being stirred. The resultant ammonia may be separated after the reaction has been completed. Preferably, however, it is removed during the reaction by means of distillation either continuously or in batch-type operation. It may be advantageous, particularly during the reaction of low-molecular alcohols under pressure, to separate the ammonia by using stripping agent, which is inert under the reaction conditions, such as a gas like nitrogen.

Subsequently, before or after removing solids by filtering, the mono-, di-, and/or polyurethane is isolated from the reaction mixture. This can be done by removing the alcohol and/or the solvent as well as the excess O-alkyl-carbamates by means of distillation, by partial distillation of the alcohol an crystallization, by crystallization, or by precipitation with or transcrystallization from other solvents. The separated O-alkyl carbamate can be recycled if so desired.

The parts referred to in the examples which follow are relative to weight. The elementary compositions and structures were confirmed by elementary analysis, mass spectroscopy, as well as infra-red and nuclear magnetic resonance spectra.

EXAMPLE 1

In a reaction vessel, 20.0 parts of 4,4'-diaminodiphenylmethane with 44 parts of n-hexyl carbamate in 60 parts of n-hexanol are heated to boiling for 12 hours with a pressure of 2 bars to 3 bars being adjusted in the reactor via a pressure valve so that the boiling temperature of hexanol is approximately 195° C. Using 25 liters of nitrogen per liter of reaction mixture an hour as a stripping agent, the ammonia formed during the reaction is continuously removed by means of distillation. Upon cooling, 18.4 parts (64.0 percent of theory relative to reacted 4,4'-diaminodiphenylmethane) of 4,4'-bis(hexoxycarbonylamino)diphenylmethane, $C_{27}H_{36}O_4N_{22}$ (molecular weight 452), crystallize, having a melting point of 142° C. to 143° C. Sixty-three percent of 4,4'-diaminodiphenylmethane has been reacted. The mother liquor still contains 4-amino-4'-(hexoxycarbonylamino)-diphenylmethane.

EXAMPLE 2

In a reaction vessel, 10.0 parts of 4,4'-diaminodiphenylmethane with 43.7 parts of octyl carbamate in 26.3 parts of octanol are heated to boiling (200° C. to 205° C.) for 2 hours. At that point, another 105 parts of octanol are added to the reaction mixture and the mixture is boiled at reflux temperature for another 15 hours. Using 10 liters of nitrogen per liter of reaction mixture an hour as a stripping agent, the ammonia formed during the reaction is continuously removed by distillation. After cooling, 7.4 parts (75.6 percent of theory) of 4,4'-bis(octoxycarbonylamino)diphenylmethane, $C_{31}H_{46}O_4N_2$ (molecular weight 510), crystallize. The melting point is 117° C. to 119° C. Thirty-eight percent of the 4,4'-diaminodiphenylmethane had been reacted. The mother liquor still contains 4-amino-4'-(octoxycarbonylamino)diphenylmethane.

EXAMPLE 3

In a reaction vessel, 12.2 parts of 2,4'-diaminotoluene with 22.3 parts of ethyl carbamate and 28 parts of ethanol are heated to boiling for 2 hours with a pressure of 8 bars to 10 bars being adjusted in the reactor via a pressure valve so that the boiling temperature of the ethanol is approximately 200° C. Using 30 liters of nitrogen per liter of reaction mixture an hour as a stripping agent, the ammonia formed during the reaction is continuously removed by means of distillation. Following this, another 140 parts of ethanol are added to the reaction mixture and the mixture is boiled at reflux temperature for another 15 hours. After completed reaction, the mixture is allowed to cool and the reactor is placed in an ice-sodium chloride mixture whereupon 13.2 parts (66.6 percent of theory) of 2,4-bis(ethoxycarbonylamino)-toluene, $C_{13}H_{18}O_4N_2$ (molecular weight 266), crystallize. The melting point is 105° C. to 108° C. The high pressure liquid chromatography analysis using the external standards method shows that 74.5 percent of the original 2,4-diaminotoluene have reacted and that residues of the 2,4-bis(ethoxycarbonylamino)toluene and a mixture of 2-amino-4-(ethoxycarbonylamino)toluene and 4-amino-2-(ethoxycarbonylamino)toluene are still present in the mother liquor.

EXAMPLE 4

In a reaction vessel, 7.9 parts of 1,5-diaminonaphthaline with 43 parts of octyl carbamate in 195 parts of octanol are heated to boiling (195° C.) for 20 hours. After cooling, a precipitate crystallizes from which 6.7 parts (75.0 percent of theory) of 1,5-bis(octoxycarbonylamino)naphthalene are obtained from transcrystallization from ethyl acetate. The melting point is 70° C. to 72° C. Thirty-eight percent of 1,5-diaminonaphthalene had been reacted.

EXAMPLE 5

In a reaction vessel, 10 parts of 4,4'-diaminodiphenylmethane with 15.2 parts of methyl carbamate in 65 parts of methanol are heated to boiling for 18 hours. A pressure of 35 bars to 37 bars is adjusted in the reactor via a pressure valve so that the boiling temperature of methanol is 180° C. to 190° C. Using 30 liters of nitrogen as a stripping agent per liter of reaction mixture an hour, the ammonia formed during reaction is continuously removed by distillation. After cooling, 10.6 parts (83.6 percent of theory) of 4,4'-bis(methoxycarbonylamino)-diphenylmethane, $C_{17}H_{18}O_4N_2$ (molecular weight 314), crystallize. The melting point is 184° C. to 186° C. Eighty percent of the 4,4-diaminodiphenylmethane has been reacted.

EXAMPLE 6

In a reaction vessel, 12.2 parts of 2,4-diaminotoluene with 42.9 parts of cyclohexyl carbamate and 200 parts of cyclohexanol are heated to boiling for 15 hours. A pressure of 2 bars to 3 bars is adjusted in the reactor via a pressure valve so that the boiling temperature of cyclohexanol is approximately 200° C. Using 15 liters of nitrogen per liter of reaction mixture an hour as a stripping agent, the ammonia formed during the reaction is continuously removed by means of distillation. After cooling, the reaction mixture is analyzed using the external standards method of high pressure liquid chromatography. This shows that 4.1 parts (29.6 percent of theory) of 2,4-bis(cyclohexoxycarbonylamino)toluene and 6.2 parts (67.6 percent of theory) of a mixture of 2-amino-4-(cyclohexoxycarbonylamino)toluene and 4-amino-2-(cyclohexoxycarbonylamino)toluene were produced. Thirty-seven percent of the 2,4-diaminotoluene was converted.

EXAMPLE 7

In a reaction vessel, 10.0 parts of a commercially available mixture of 2,2'-, 2,4'- and 4,4'-diaminodiphenylmethane and polyphenylpolymethylene polyamines with 23 parts of ethyl carbamate in 30 parts of ethanol are heated to boiling for 15 hours. The pressure in the reactor is adjusted to 7 bars to 9 bars via a pressure valve so that the boiling temperature of the ethanol is approximately 195° C. Using 25 liters of nitrogen per liter of reaction mixture an hour as a stripping agent, the ammonia formed during the reaction is continuously removed by means of distillation. The mixture is allowed to cool and excess ethanol and excess ethylcarbamate are distilled under vacuum until a sump temperature of 190° C. is reached. The residue is mixed with 100 parts of cyclohexane and is agitated resulting in a powdery precipitate which is separated and analyzed by means of high pressure liquid choromatography. The analysis shows that the mixture of 2,4'-, 2,2'-, and 4,4'-bis(ethoxycarbonylamino)diphenylmethane and polyphenylpolymethylenepolyethylurethane had been formed.

EXAMPLE 8

In a reaction vessel, 60 parts of aniline with 192 parts of butyl carbamate, 39 parts of urea and 140 parts of butanol are heated to boiling for 6 hours. A pressure of 5 bars to 6.5 bars is adjusted in the reactor via a pressure valve so that the boiling temperature is approximately 190° C. Using 20 liters of nitrogen as a stripping agent per liter of reaction mixture an hour, the ammonia formed during the reaction is continuously removed by means of distillation. After completed reaction, the unreacted aniline, excess butanol and excess butyl carbamate are removed by distillation under reduced pressure of approximately 20 millibars. By distillation at 0.05 millibars at 140° C. to 142° C., 87 parts of phenylbutylurethane (94.4 percent of theory relative to reacted aniline) are subsequently obtained. Seventy-four percent of the aniline had been reacted.

EXAMPLE 9

In a reaction vessel, 93 parts of aniline with 350 parts of methyl carbamate and 96 parts of methanol are heated to 175° C. for 6 hours. A pressure of 5 bars to 6 bars in the reactor is adjusted via a pressure valve. The ammonia formed during the reaction is removed by batch-type distillation. After completed reaction, the reaction mixture is subjected to fractional distillation resulting in 109 parts of phenylmethylurethane (85 percent of theory relative to reacted aniline) in addition to unreacted aniline, excess methanol and methyl carbamate. The melting point is 54° C. to 55° C. Eighty-five percent of the aniline was reacted.

EXAMPLE 10

In a reaction vessel, 120 parts of 3,5-dichloroaniline with 280 parts of methyl carbamate and 75 parts methanol are heated to 185° C. for 18 hours. A pressure of 9 bars to 10 bars in the reactor is adjusted via a pressure valve. Using 30 liters of nitrogen as a stripping agent per liter of reaction mixture an hour, the ammonia formed during the reaction is removed by continuous distillation. After completed reaction, the reaction solution is analyzed by gas chromatography using the internal standard method. It is found that 94 parts of 3,5-dichlorophenylmethylurethane was formed (83.6 percent of theory relative to reacted 3,5-bis-chloroaniline). The melting temperature is 118° C. to 120° C. Sixty-nine percent of the 3,5-dichloroaniline was reacted.

EXAMPLE 11

In a reaction vessel, 15.2 parts of 2-amino-4-nitrotoluene with 40 parts of methyl carbamate and 10 parts of methanol are heated to 190° C. for 20 hours. Via a pressure valve, the pressure in the reactor is adjusted to 7 bars to 9 bars. Using 15 liters of nitrogen as a stripping agent per liter of reaction mixture an hour, the ammonia formed during the reaction is removed by continuous distillation. After completed reaction, the reaction solution is analyzed by means of high pressure liquid chromatography using the external standard method. It was found that 15 parts of 2-methoxycarbonylamino-4-nitrotoluene are formed (96.5 percent of theory relative to reacted 2-amino-4-nitrotoluene). The melting point is 133° C. to 134° C. Seventy-four percent of the 2-amino-4-nitrotoluene was reacted.

EXAMPLE 12

In a reaction vessel, 21 parts of 4-aminotoluene with 11.8 parts of urea, 70 parts of ethyl carbamate and 36 parts of ethanol are heated to 185° C. for 10 hours. Via a pressure valve, the pressure in the reactor is adjusted to 7 bars to 9 bars. Using 20 liters of nitrogen as a stripping agent per liter of reaction mixture an hour, the ammonia formed during the reaction is removed by continuous distillation. After completed reaction, unreacted 4-aminotoluene, excess ethanol and excess ethyl carbamate are removed by distillation under reduced pressure of approximately 18 millibars. By means of another distillation at 0.1 millibar and 125° C. to 130° C., 30 parts of 4-ethoxycarbonylaminotoluene are obtained (97 percent of theory relative to reacted 4-aminotoluene). The melting point is 55° C. to 57° C. Eighty-eight percent of 4-aminotoluene was reacted.

EXAMPLE 13

In a reaction vessel, 22 parts of 3-aminophenol with 100 parts of ethyl carbamate, 12 parts of urea and 45 parts of ethanol are heated to 185° C. for 10 hours with the pressure in the reactor being adjusted to 7 bars to 8 bars via a pressure valve. Using 20 liters of nitrogen as a stripping agent per liter of reaction mixture an hour, the ammonia formed during the reaction is removed by distillation. After completed reaction, excess ethanol and excess ethyl carbamate are removed by distillation under a vacuum of approximately 15 millibars. The residue is poured into 10 percent sodium hydroxide solution until everything is dissolved and the solution is subsequently adjusted to a pH of 5 using 10 percent sulfuric acid. Formed were 23.3 parts of 3-ethoxycarbonylaminophenol precipitate (63.8 percent of theory relative to the 3-aminophenol). The melting point is 99° C. to 100° C.

EXAMPLE 14

In a reaction vessel, 10 parts of 4,4'-diaminodiphenylmethane with 15.2 parts of methyl carbamate and 6 parts of urea in 35 parts methanol are heated to 185° C. to 190° C. for 6 hours with a pressure of 24 bars to 27 bars being adjusted in the reactor via a pressure valve. Using 30 liters of nitrogen as a stripping agent per liter of reaction mixture an hour, the ammonia formed during the reaction is removed by continuous distillation. After cooling, 14 parts of 4,4'-bis(methoxycarbonylamino)diphenylmethane crystallize (88.3 percent of theory relative to reactant 4,4'-diaminodiphenylmethane). The melting point is 184° C. to 185° C. The conversion of 4,4'-diaminodiphenylmethane is essentially quantitative. Still present in the mother liquor is 4-amino-4'-(methoxycarbonylamino)diphenylmethane.

The embodiments of the invention in which an exclusive privilege or property is claimed are as follows:

1. A process for the preparation of an aryl mono-, di-, and/or polyurethane comprising the steps of
   A. reacting a primary aromatic mono-, di- and/or polyamine with a carbamate of the formula $H_2N\text{-}COOR$ in which R represents an unsubstituted or substituted aliphatic, cycloaliphatic or aromatic-aliphatic radical in the presence of an alcohol at temperatures greater than 160° C., and
   B. separating the ammonia and other by-products from the aryl mono-, di-, and/or polyurethane.

2. The process of claim 1 carried out in the presence of urea with the mole ratio of urea to alcohol being equal to or less than 1.

3. The process of claim 2 wherein a maximum of 1.5 equivalent of urea relative to the amino groups of the mono-, di- and polyamine is used in addition to the carbamate.

4. The process of claim 1 wherein the reactants are present in such quantities that the ratio of amino groups of the primary aromatic mono-, di- and/or polyamines to carbamate to hydroxyl groups of the alcohol is 1:0.5–20:1–100.

5. The process of claim 1 or 2 wherein the monoamine is selected from the group consisting of aniline, 3-hydroxyaniline and 3,5-dichloroaniline are used as primary aromatic monoamines.

6. The process of claim 1 or 2 wherein the diamine is selected from the group consisting of 2,4- and 2,6-diaminotoluene, the corresponding isomer mixtures thereof, 1,5-diaminonaphthalene, 3,3'-ditoluene-4,4'-diamine, 2,2'-, 2,4'- and 4,4'-diaminodiphenylmethane and the corresponding isomer mixtures thereof.

7. The process of claim 1 or 2 wherein the polyamine is a mixture of diaminodiphenylmethanes and polyphenylpolymethylene polyamine.

8. The process of claim 1 or 2 wherein the ammonia by-product is continuously separated from the system as it is formed.

9. The process of claim 1 or 2 wherein the reaction is carried out at pressures of 0.1 bar to 120 bars.

10. Process according to claim 1 or 2 wherein the carbamates used are those of carbamic acid and aliphatic and cycloaliphatic monoalcohols having 1 to 10 carbon atoms in the alcohol radical.

11. A process for the preparation of an aryl mono-, di-, and/or polyurethane comprising reacting a primary aromatic amine with an unsubstituted carbamic acid ester in the presence of an alcohol and an urea at a temperature of greater than 160° C.

12. A process for the preparation of an aryl mono-, di-, and/or polyurethane which comprises reacting a primary aromatic mono-, di-, and/or polyamine with an unsubstituted carbamic acid ester in the presence of an alcohol at temperatures greater than 160° C.

* * * * *